(12) United States Patent
Niazi et al.

(10) Patent No.: US 9,885,704 B2
(45) Date of Patent: Feb. 6, 2018

(54) REAGENTS AND METHODS FOR CANCER TREATMENT AND PREVENTION

(71) Applicant: The Buck Institute For Age Research, Novato, CA (US)

(72) Inventors: Kayvan R. Niazi, Los Angeles, CA (US); Shahrooz Rabizadeh, Los Angeles, CA (US); Dale E. Bredesen, Novato, CA (US)

(73) Assignee: The Buck Institute for Age Research, Novato, CA (US)

( * ) Notice: Subject to any disclaimer, the term of this patent is extended or adjusted under 35 U.S.C. 154(b) by 52 days.

(21) Appl. No.: 14/800,412

(22) Filed: Jul. 15, 2015

(65) Prior Publication Data

US 2016/0069864 A1 Mar. 10, 2016

Related U.S. Application Data

(62) Division of application No. 11/389,695, filed on Mar. 27, 2006, now Pat. No. 9,107,863.

(51) Int. Cl.
| | | |
|---|---|---|
| *G01N 33/00* | (2006.01) | |
| *G01N 33/50* | (2006.01) | |
| *A61K 31/365* | (2006.01) | |
| *A61K 39/00* | (2006.01) | |

(52) U.S. Cl.
CPC ....... *G01N 33/5023* (2013.01); *A61K 31/365* (2013.01); *A61K 39/0011* (2013.01); *A61K 2039/5154* (2013.01); *G01N 2333/90241* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 2001/0033839 A1* | 10/2001 | Barbera-Guillem . | A61K 39/395 424/130.1 |
| 2002/0137799 A1 | 9/2002 | Gould et al. | |
| 2003/0175297 A1 | 9/2003 | Urashima | |
| 2003/0212026 A1 | 11/2003 | Krieg et al. | |
| 2003/0235818 A1 | 12/2003 | Katritch et al. | |
| 2005/0214888 A1 | 9/2005 | Morita et al. | |

FOREIGN PATENT DOCUMENTS

| | | |
|---|---|---|
| WO | 2003/020371 A2 | 3/2003 |
| WO | 2005/051423 A2 | 6/2005 |

OTHER PUBLICATIONS

Ting et al (EMBO, 15(22):6189-6196, 1996).*
Shatrov et al (BPRC (234:121-124, 1997).*
Miller et al (RR, 151:310-318, 1999).*
Lasek et al (CCP, 50:213-222, 2002).*
Kabahima et al (FEBS Letters 578:36-40, 2004).*
Sheth et al (I, 63:483-490, 1988).*
Rutenfranz et al (Blut, 61(1):30-37, 1990, abstract only).*
Norgard et al (II, 64(9):3845-3852, 1996).*
Delpino et al., Protein synthesis in TE 671/RD (human rabdomiosarcoma) cells treated with thapsigargin and hyperthermia: impairment of HSP 70 induction, Journal of Biological Regulators and Homeostatic Agents, vol. 9, No. 4, pp. 132-138, Oct.-Dec. 1995.
Heike et al., Stress Protein/Peptide Complexes Derived from Autologous Tumor Tissue as Tumor Vaccines, Biochemical Pharmacology, vol. 58, pp. 1381-1387, 1999.
Kalai et al., Regulation of the expression and processing of caspase-12, The Journal of Cell Biology, vol. 162, No. 3, pp. 457-467, Aug. 4, 2003.
Makunga et al., Micropropagation of Thapsia garganica—a medicinal plant, Plant Cell Rep 21: pp. 967-973, 2003.
Minev, Melanoma Vaccines, Seminars in Oncology, vol. 29, No. 5: pp. 479-493, Oct. 2002.
Muthukkumar et al., Role of EGR-1 in Thapsigargin-Inducible Apoptosis in the Melanoma Cell Line A375-C6, Molecular and Cellular Biology, vol. 15, No. 11, p. 6262-6272, Nov. 1995.
Reap et al., Radiation and stress-induced apoptosis: A role for Fas/Fas ligand interactions, Proc. Natl. Acad. Sci. USA vol. 94, pp. 5750-5755, May 1997.
Wong et al., Inhibition of protein synthesis and early protein processing by thapsigargin in cultured cells, Biochem J. ; 289(Pt 1): 71-79, Jan. 1, 1993.
Ying et al., Colocalization of Ca2+-ATPase and GRP94 with p58 and the effects of thapsigargin on protein recycling suggest the participation of the pre-Golgi intermediate compartment in intracellular Ca2+ storage, European Journal of Cell Biology 81, pp. 469-483, Sep. 2002.
Takei M. et al. "T-cadinol and calamenene induce dendritic cells from human monocytes and drive Th1 polarization" European Journal of Pharmacology, Elsevier Science, NL, vol. 537, No. 1-3, Mar. 3, 2006, pp. 190-199.
Kmonickova E et al. , "Immunostimulatory activity of sarco/endoplasmic reticulum Ca2+-ATPases Inhibitors, thapsigargin and trilobolide", Fundamental & Clinical Pharmacology, Elsevier, vol. 22, No. Suppl. 2, Aug. 1, 2008, p. 84.

(Continued)

*Primary Examiner* — Brad Duffy
(74) *Attorney, Agent, or Firm* — Lucas & Mercanti, LLP

(57) ABSTRACT

The invention generally relates to the prevention and/or treatment of cancer, and, more specifically, to the treatment of tumors, including solid tumors and their metastases, without radiation or standard chemotherapeutic agents. In one embodiment, the invention involves a method comprising: a) providing a subject with tumor cells, b) removing at least a portion of said tumor cells from said subject to create removed cells, c) treating at least a portion of said removed cells ex vivo, using stimulating agents, including thapsigargin and/or thapsigargin-related compounds, so as to create treated tumor cells; and d) introducing said treated tumor cells (or fragments thereof) in vivo into the same subject to generate anticancer therapeutic effects.

13 Claims, 14 Drawing Sheets

(56) References Cited

OTHER PUBLICATIONS

Ramanathapuram L.V. et al., "Vesiculated alpha-tocopheryl succinate enhances the anti-tumor effect of dendritic cell vaccines", Cancer immunology, immunotherapy, Feb. 2006, vol. 55, No. 2, pp. 166-177.
Gollnick S. O. et al., "Generation of Effective Antitumor Vaccines Using Photodynamic Therapy", Cancer research, 2002, vol. 62, No. 6, pp. 1604-1608.
Translation of "Notice of Reasons for Rejection" dated Sep. 24, 2014, for JP Patent Application No. 2013-170115 (2 pages).
Extended European Search Report dated Oct. 9, 2015, for EP Patent Application No. 1580408.5 (15 pages).

\* cited by examiner

| Cancer Type or Tissue of Origin: | Lines Inducing Significant Inflammatory Cytokine Release Relative to Sample Size: |
|---|---|
| Breast | (2/2) |
| Colon | (5/6) |
| Endothelium | (1/1) |
| Lung Carcinoma | (1/2) |
| Neuroblastoma | (1/1) |
| Osteosarcoma | (1/1) |
| Prostate | (3/3) |

Figure 3

Panel A
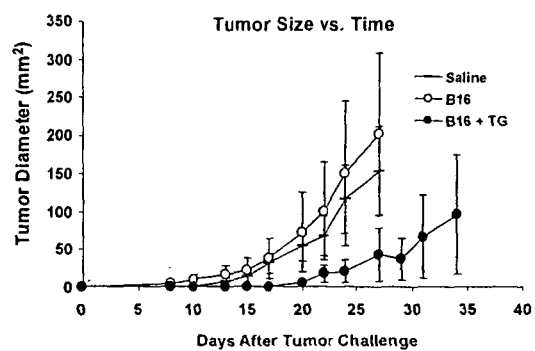
Panel B
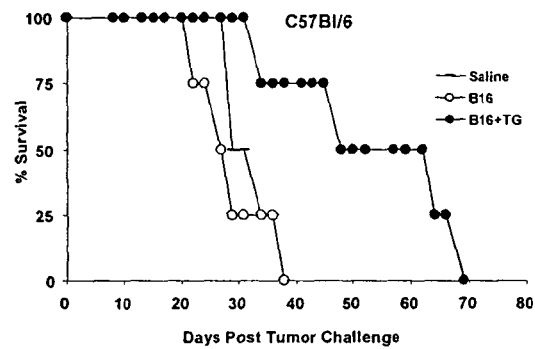
Figure 4

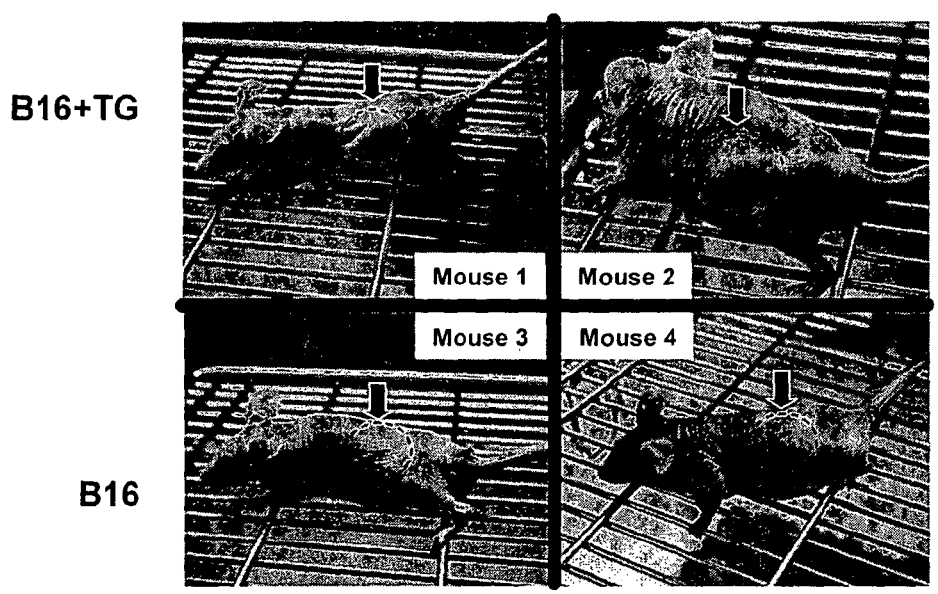
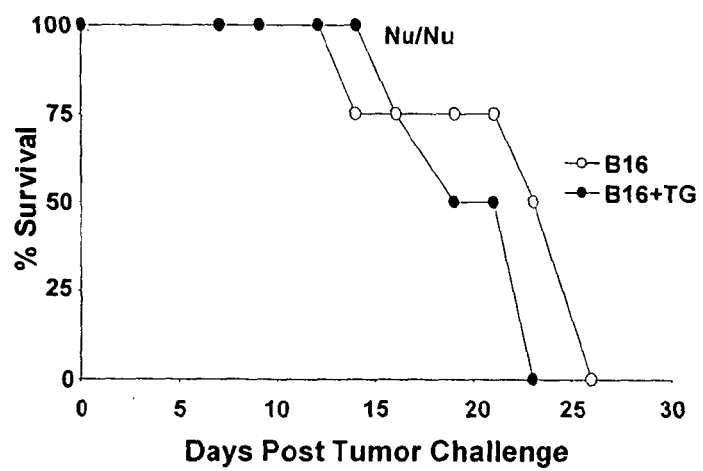
Figure 5

Panel A
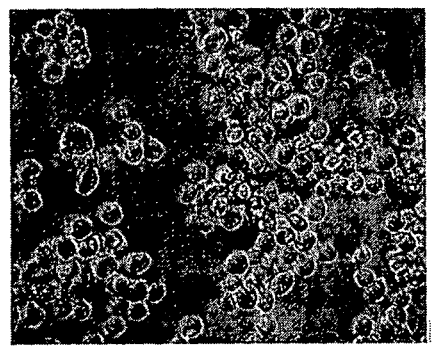
Panel B
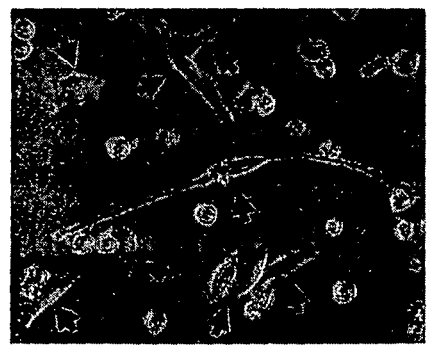
Figure 8

Panel A
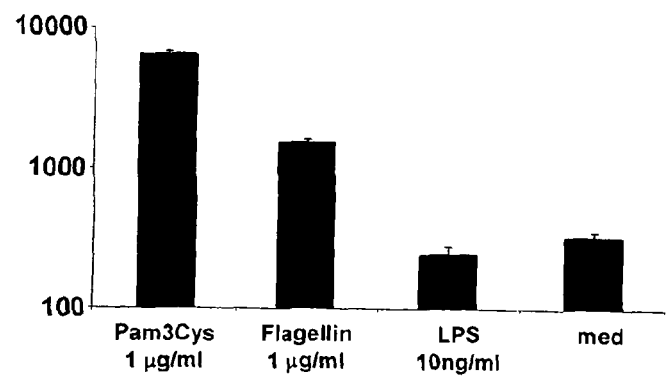
Panel B
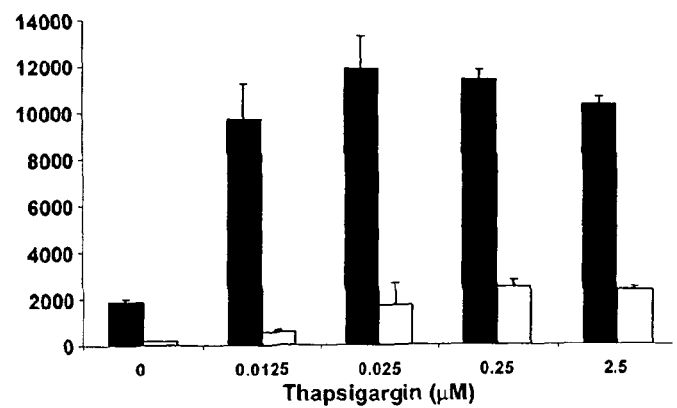
Figure 10

CD40L nucleotide sequence:
ATGATAGAAACATACAGCCAACCTTCCCCCAGATCCGTGGCAACTGGACTTCCAGCGAGCATGAAGATTTTATGTATTACTTACTGT
TTTCCTTATCACCCAAATGATTGGATCTGTGCTTTTTGCTGTGTATCTTCATAGAAGATTGATAAGGTCGAAGAGGAAGTAAACCTTC
ATGAAGATTTTGTATTCATAAAAAGCTAAAGAGATGCAACAAAGGAGAAGGATCTTTATCCTTGCTGAACTGTGAGGAGATGAGAAGG
CAATTTGAAGACCTTGTCAAGGATATAACGTTAAACAAGAAAAAACAGCTTTGAAATGCAAAGAGGTGATGAGGATCC
TCAAATTGCAGCACACGTTGTAAGCGAAGCCAACAGTAATGCAGCATCCGTTCTACAGTGGGCCAAGAAAGGATATTATACCATGAAAA
GCAACTTGGTAATGCTTGAGTCAACAGCTGAAAATGGGAAACAGCTGACGGTTAAAAGAGAAGGACTCTATTATGTCTACACTCAAGTCT
AATCGGGAGCCTTCAACGCCCATTCATCGTCGGCCTCTGGCTGAAGCCCAGCAGTGTTCACTTGGGCGAGTCTGTTGAATTACAAGCT
AAATACCCACAGTTCCTCCCCAGCTTTGCGAGCAGCAGTTGGCTTCACTTGGGCGAGTGTTCACTTGGCGGTCTGGTGCTTCTGTGTTTG
TCAACGTGACTGAAGCAAGCCAAGTGATCCACAGAGTTGGCTTCTCATCTTTTGGCTTACTCAAACTCTGA

Comments for pVAX1©:
2999 bp

CMV promoter: bases 137-724
T7 promoter/priming site: bases 664-683
Multiple cloning site: bases 696-811
BGH reverse priming site: bases 823-840
BGH polyadenylation signal: bases 829-1053
Kanamycin resistance gene: bases 1226-2020
pUC origin: bases 2320-2993

SEQUENCE LISTING

<160> NUMBER OF SEQ ID NOS: 3

<210> SEQ ID NO 1
<211> LENGTH: 783
<212> TYPE: DNA
<213> ORGANISM: Mus musculus

<400> SEQUENCE: 1

```
atgatagaaa catacagcca accttccccc agatccgtgg caactggact tccagcgagc      60
atgaagattt ttatgtattt acttactgtt ttccttatca cccaaatgat tggatctgtg     120 cttttgctg tgtatcttca tagaagattg gataaggtcg aagaggaagt aaaccttcat      180
gaagattttg tattcataaa aaagctaaag agatgcaaca aaggagaagg atctttatcc     240
ttgctgaact gtgaggagat gagaaggcaa tttgaagacc ttgtcaagga tataacgtta     300
aacaaagaag agaaaaaaga aaacagcttt gaaatgcaaa gaggtgatga ggatcctcaa     360
attgcagcac acgttgtaag cgaagccaac agtaatgcag catccgttct acagtgggcc     420
aagaaaggat attataccat gaaaagcaac ttggtaatgc ttgaaaatgg gaaacagctg     480
acggttaaaa gagaaggact ctattatgtc tacactcaag tcaccttctg ctctaatcgg     540
gagccttcga gtcaacgccc attcatcgtc ggcctctggc tgaagcccag cagtggatct     600
gagagaatct tactcaaggc ggcaaatacc cacagttcct cccagctttg cgagcagcag     660
```

```
tctgttcact tgggcggagt gtttgaatta caagctggtg cttctgtgtt tgtcaacgtg    720
actgaagcaa gccaagtgat ccacagagtt ggcttctcat cttttggctt actcaaactc    780
tga                                                                  783

<210> SEQ ID NO 2
<211> LENGTH: 795
<212> TYPE: DNA
<213> ORGANISM: Mus musculus
<220> FEATURE:
<221> NAME/KEY: CDS
<222> LOCATION: (7)..(786)

<400> SEQUENCE: 2 tctaga atg ata gaa aca tac agc caa cct tcc ccc aga tcc gtg gca         48
       Met Ile Glu Thr Tyr Ser Gln Pro Ser Pro Arg Ser Val Ala
       1               5                  10 act gga ctt cca gcg agc atg aag att ttt atg tat tta ctt act gtt       96
Thr Gly Leu Pro Ala Ser Met Lys Ile Phe Met Tyr Leu Leu Thr Val
15                  20                  25                  30 ttc ctt atc acc caa atg att gga tct gtg ctt ttt gct gtg tat ctt      144
Phe Leu Ile Thr Gln Met Ile Gly Ser Val Leu Phe Ala Val Tyr Leu
                35                  40                  45 cat aga aga ttg gat aag gtc gaa gag gaa gta aac ctt cat gaa gat      192
His Arg Arg Leu Asp Lys Val Glu Glu Glu Val Asn Leu His Glu Asp
            50                  55                  60 ttt gta ttc ata aaa aag cta aag aga tgc aac aaa gga gaa gga tct      240
Phe Val Phe Ile Lys Lys Leu Lys Arg Cys Asn Lys Gly Glu Gly Ser
65                  70                  75 tta tcc ttg ctg aac tgt gag gag atg aga agg caa ttt gaa gac ctt      288
Leu Ser Leu Leu Asn Cys Glu Glu Met Arg Arg Gln Phe Glu Asp Leu
            80                  85                  90 gtc aag gat ata acg tta aac aaa gaa gag aaa aaa gaa aac agc ttt      336
Val Lys Asp Ile Thr Leu Asn Lys Glu Glu Lys Lys Glu Asn Ser Phe
95                  100                 105                 110 gaa atg caa aga ggt gat gag gat cct caa att gca gca cac gtt gta      384
Glu Met Gln Arg Gly Asp Glu Asp Pro Gln Ile Ala Ala His Val Val
                115                 120                 125 agc gaa gcc aac agt aat gca gca tcc gtt cta cag tgg gcc aag aaa      432
Ser Glu Ala Asn Ser Asn Ala Ala Ser Val Leu Gln Trp Ala Lys Lys
            130                 135                 140 gga tat tat acc atg aaa agc aac ttg gta atg ctt gaa aat ggg aaa      480
Gly Tyr Tyr Thr Met Lys Ser Asn Leu Val Met Leu Glu Asn Gly Lys
145                 150                 155 cag ctg acg gtt aaa aga gaa gga ctc tat tat gtc tac act caa gtc      528
Gln Leu Thr Val Lys Arg Glu Gly Leu Tyr Tyr Val Tyr Thr Gln Val
            160                 165                 170 acc ttc tgc tct aat cgg gag cct tcg agt caa cgc cca ttc atc gtc      576
Thr Phe Cys Ser Asn Arg Glu Pro Ser Ser Gln Arg Pro Phe Ile Val
175                 180                 185                 190 ggc ctc tgg ctg aag ccc agc agt gga tct gag aga atc tta ctc aag      624
Gly Leu Trp Leu Lys Pro Ser Ser Gly Ser Glu Arg Ile Leu Leu Lys
                195                 200                 205 gcg gca aat acc cac agt tcc tcc cag ctt tgc gag cag cag tct gtt      672
Ala Ala Asn Thr His Ser Ser Gln Leu Cys Glu Gln Gln Ser Val
            210                 215                 220 cac ttg ggc gga gtg ttt gaa tta caa gct ggt gct tct gtg ttt gtc      720
His Leu Gly Gly Val Phe Glu Leu Gln Ala Gly Ala Ser Val Phe Val
225                 230                 235 aac gtg act gaa gca agc caa gtg atc cac aga gtt ggc ttc tca tct      768
Asn Val Thr Glu Ala Ser Gln Val Ile His Arg Val Gly Phe Ser Ser
```

```
Asn Val Thr Glu Ala Ser Gln Val Ile His Arg Val Gly Phe Ser Ser
    240                 245                 250 ttt ggc tta ctc aaa ctc tgatctaga                                    795
Phe Gly Leu Leu Lys Leu
255                 260

<210> SEQ ID NO 3
<211> LENGTH: 260
<212> TYPE: PRT
<213> ORGANISM: Mus musculus
<220> FEATURE:
<223> OTHER INFORMATION: Synthetic

<400> SEQUENCE: 3

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
                20                  25                  30

Ile Thr Gln Met Ile Gly Ser Val Leu Phe Ala Val Tyr Leu His Arg
            35                  40                  45

Arg Leu Asp Lys Val Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
    210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
            260
```

REAGENTS AND METHODS FOR CANCER TREATMENT AND PREVENTION

This application is a divisional application of allowed U.S. application Ser. No. 11/389,695, filed Mar. 27, 2006, which is hereby incorporated by reference in its entirety.

FIELD OF THE INVENTION

The invention generally relates to the treatment of cancer, and, more specifically, to the treatment of tumors, including solid tumors and their metastases, without radiation or standard chemotherapeutic agents. In a preferred embodiment, the invention relates to the prevention and treatment of cancer through use of a cancer vaccine.

BACKGROUND

Modern cancer therapy largely involves the use of radiation, surgery and chemotherapeutic agents. However, results with these measures, while beneficial in some tumors, has had only marginal or no effect in many others. Furthermore, these approaches often have unacceptable toxicity.

Both radiation and surgery suffer from the same theoretical drawback. It has been recognized that, given that a single clonogenic malignant cell can give rise to sufficient progeny to kill the host, the entire population of neoplastic cells must be eradicated. See generally, Goodman and Gilman *The Pharmacological Basis of Therapeutics* (Pergamon Press, 8th Edition) (pp. 1202-1204). This concept of "total cell kill" implies that total excision of a tumor is necessary for a surgical approach, and complete destruction of all cancer cells is needed in a radiation approach, if one is to achieve a cure. In practice this is rarely possible; indeed, where there are metastases, it is impossible.

Moreover, traditional chemotherapeutic cancer treatments also rarely result in complete remission of the tumor, and the significant dosage levels required to generate even a moderate response are often accompanied by unacceptable toxicity. Anticancer agents typically have negative hematological effects (e.g., cessation of mitosis and disintegration of formed elements in marrow and lymphoid tissues), and immunosuppressive action (e.g., depressed cell counts), as well as a severe impact on epithelial tissues (e.g., intestinal mucosa), reproductive tissues (e.g., impairment of spermatogenesis), and the nervous system. P. Calabresi and B. A. Chabner, In: Goodman and Gilman *The Pharmacological Basis of Therapeutics* (Pergamon Press, 8th Edition) (pp. 1209-1216). The high dosage levels, and the resulting toxicity, are in large part necessitated by the lack of target specificity of the anticancer agents themselves. The drug needs to distinguish between host cells that are cancerous and host cells that are not cancerous. The vast bulk of anticancer drugs are indiscriminate at this level, and have significant inherent toxicity.

Success with standard chemotherapeutics as anticancer agents has also been hampered by the phenomenon of multiple drug resistance, resistance to a wide range of structurally unrelated cytotoxic anticancer compounds. J. H. Gerlach et al., *Cancer Surveys*, 5:25-46 (1986). The underlying cause of progressive drug resistance may be due to a small population of drug-resistant cells within the tumor (e.g., mutant cells) at the time of diagnosis. J. H. Goldie and Andrew J. Coldman, *Cancer Research*, 44:3643-3653 (1984). Treating such a tumor with a single drug first results in a remission, where the tumor shrinks in size as a result of the killing of the predominant drug-sensitive cells. With the drug-sensitive cells gone, the remaining drug-resistant cells continue to multiply and eventually dominate the cell population of the tumor.

Treatment at the outset with a combination of drugs was proposed as a solution, given the small probability that two or more different drug resistances would arise spontaneously in the same cell. V. T. DeVita, Jr., *Cancer*, 51:1209-1220 (1983). However, it is now known that drug resistance is due to a membrane transport protein, "P-glycoprotein," that can confer general drug resistance. M. M. Gottesman and I. Pastan, *Trends in Pharmacological Science*, 9:54-58 (1988). Phenotypically, the tumor cells show, over time, a reduced cellular accumulation of all drugs. In short, combination chemotherapy appears not to be the answer.

Adoptive cellular immunotherapy has been proposed as an alternative treatment methodology, using the body's own immune system in an attempt to improve target cell specificity while reducing toxicity. The activation and proliferation of various lymphocyte populations with lymphokines both in vivo and in vitro has been investigated, with mixed degrees of success. For example, lymphokine-activated killer (LAK) cells and tumor-infiltrating lymphocytes (TILs) have both been used in combination with interleukin-2 (IL-2) in the treatment of metastatic disease. See Rosenberg et al., *N. Engl. J. Med.* 316:889-97 (1987); Belldegrun et al., *Cancer Res* 48:206-14 (1988).

Unfortunately, the inclusion of high levels of IL-2 to activate and expand the cell populations is itself associated with significant toxicity to the patient. Moreover, target-cell specific cell populations have been difficult to expand in vitro, since lymphocytes cultured in high levels of IL-2 eventually develop an unresponsiveness to IL-2, and subsequently exhibit a serious decline in proliferation and cytotoxicity. See Schoof et al., *Cancer Res.* 50: 1138-43 (1990). The latter problem has also impeded efforts to successfully use lymphocytes as cellular vehicles for gene therapy in man.

What is needed is a specific anticancer approach that is reliably tumoricidal to a wide variety of tumor types. Importantly, the treatment must be effective with minimal host toxicity.

SUMMARY OF THE INVENTION

The invention generally relates to the prevention and/or treatment of cancer, and, more specifically, to the treatment of tumors, including solid tumors and their metastases, without radiation or standard chemotherapeutic agents. In one embodiment, the invention involves a method comprising: a) providing a subject with tumor cells, b) removing at least a portion of said tumor cells from said subject to create removed cells, c) treating at least a portion of said removed cells ex vivo, using stimulating agents, including thapsigargin and/or thapsigargin-related compounds, so as to create treated tumor cells; and d) introducing said treated tumor cells in vivo into the same subject to generate anticancer therapeutic effects. Prior to introducing said treated tumor cells, they may be washed (e.g. with buffer, culture medium, etc.) to minimize the amount of the agent carried over into the subject. In a preferred embodiment, the invention comprises a method comprising: a) providing a patient with tumor cells, b) removing at least a portion of said tumor cells from said patient to create removed cells, c) exposing at least a portion of said removed cells ex vivo to an agent selected from the group consisting of thapsigargin and thapsigargin-related compounds, so as to create treated tumor cells; d) lysing said treated tumor cells to create cell fragments, and e) introducing said fragments in vivo into the same patient to generate an anticancer therapeutic effect. It is preferred that in one embodiment, prior to step (d), the treated cells are washed so as to minimize the amount of agent carried over into the next step. It is not intended that the present invention be limited by any particular exposure/treatment time for step (c). A variety of exposure times is contemplated, including exposure times between 1 second and 72 hours, more preferably between 30 seconds and 1 hour, still more preferably 1 minute and 30 minutes. It is not intended that the present invention be limited by the nature of the lysing in step (d). In one embodiment, the treated tumor cells are lysed by freeze/thawing the cells. In another embodiment, a lysis agent is used; lysis agents can be detergents (e.g. sodium dodecyl sulfate), enzymes (e.g. an enzyme digestion buffer made up of 1 ml of Qiagen Buffer B1, 20 µl of lysozyme, 45 µl of protease and 0.35 ml of Qiagen Buffer B2), or simple solutions (e.g. phosphate buffer saline) or more complex solutions for lysing cells osmotically, e.g. in hypotonic lysis buffer (5 mM sodium phosphate pH 7.4, protease inhibitor cocktail, 5 mM DTT). In another embodiment, the cells are sonicated. In another embodiment, a cell extract is made (e.g. a membrane extract, a cytoplasmic extract, etc.). In still other embodiments, combinations of these methods are used (e.g. hypotonic lysis followed by treatment with a homogenizer, (e.g. Polytron® PT 3000, Kinematica, Luzern, Switzerland). It is not intended that the present invention be limited to how the cell fragments or cell components are introduced; they can be administered intravenously, intramuscularly, intraperitoneally, subcutaneously, intradermally, etc. It may be preferred to administer the fragments/extracts in certain ways for certain cancers. For example, in the case of skin cancer, it may be preferred (in one embodiment) to administer the fragment/extracts through the skin (e.g. subcutaneously, transdermally, etc.) to treat such cancers as melanoma. In the case of prostate cancer, it may be preferred (in one embodiment) to administer the fragments/extracts intraperitoneally. On the other hand, in some embodiments, the fragments/extracts are administered to a site that is distant from the tumor and into a tissue (e.g. muscle, skin, etc.) that is unrelated to the tissue type of the tumor (e.g. breast cancer, lung cancer, etc.).

It is also not intended that the present invention be limited to introducing only fragments/extracts in vivo; other compounds (including but not limited to, adjuvants, mitogens and the like) or components (including but not limited to expression constructs providing continuous or transient expression of peptides, polypeptides or proteins, or constructs that provide continuous or transient generation of nucleic acid molecules). With regard to other compounds, the present invention contemplates in one embodiment, the administration of one or more cytokines before, after, or together with the fragments/extracts. In still other embodiments, the patient may be treated before, after or at the same time with one or more drugs that stimulate production of white blood cells in the bone marrow, such as the granulocyte-macrophage colony stimulating factor (GM-CSF, generic name sargramostim, brand name Leukine®) and granulocyte colony stimulating factor (G-CSF, generic name filgrastim, brand name Neupogen®). With regard to preferred expression constructs, in one embodiment, the present invention contemplates introducing a CD40L expression plasmid before, after, or together with the fragment/extracts in order to create a long-lasting effect.

It is preferred, in one embodiment, that the fragments/extracts are cell free, in order to avoid the reintroduction of live cancer cells into the patient (however, it may be possible in some cases to reintroduce cells, rather than extracts, or extracts that contain cells, because they rapidly die or are rapidly destroyed by the patient). In one embodiment, said tumor cells are obtained from a biopsy and the extracts are administered to the same patient. In another embodiment, the fragments/extracts are introduced into a different patient (indeed, the fragment/extracts may be used widely on a plurality of patients). In still a third embodiment, the cells are established as a cell line for continuous anticancer use; in other words, in this third embodiment, tumor cells are not taken from a patient each time they are needed, but are, instead, provided from a cell line (usually the same cancer type as the patient's tumor). The cell line can be stored in appropriate containers under liquid nitrogen using conventional techniques (e.g., DMSO, culture media, fetal calf serum, etc.). On the other hand, they may be passed continuously in culture until use. It is not intended that the present invention be limited to the particular type of cancer. A variety of cancer types are contemplated, including but not limited to skin cancer cells, prostate cancer cells, breast cancer cells, cervical cancer cells, uterine cancer cells, pancreatic cancer cells, colon cancer cells, lung cancer cells, bone cancer cells and lymphomas (see Table 1 for a list of illustrative cell lines). It is not intended that the present invention be limited to a single treatment, i.e. the fragments/extracts (with or without other compounds or components) can be administered at intervals (e.g. once per week, twice per month, once per month, once every six months, once per year, etc.).

It is contemplated in some embodiments where the tumor cells are removed from the patient, that a) standard surgery for the removal of a primary tumor (or portion thereof) is used. After b) treating the tumor cells ex vivo, using stimulating agents, including thapsigargin and/or thapsigargin-related compounds, so as to create treated tumor cells; c) preparing tumor cell fragments/extracts from said treated tumor cells, and d) introducing said fragments/extracts in vivo into the same patient, it is contemplated that an anti-metastases effect is generated. In this manner, embodiments of the present invention can be combined with conventional surgical procedures. For example, in one embodiment, a primary tumor in the breast may be removed by conventional surgery (i.e. partial or complete mastectomy), and the fragments/extracts may be

TABLE 1

Designation And Origin Of Human Cell Lines And Strains[1]

| ORIGIN | CELL LINES OR STRAINS |
|---|---|
| Colonic carcinoma | SW1116, HCT116, SKCO-1, HT-29, KM12C, KM12SM, KM12L4, SW480 |
| Pancreatic carcinoma | BxPC-3, AsPC-1, Capan-2, MIA PaCa-2, Hs766T |
| Colon adenoma | VaCo 235 |
| Lung carcinoma | A549 |
| Prostate carcinoma | PC-3, DU-145 |
| Breast carcinoma | 009P, 013T |
| Lymphoma | Daudi, Raji |
| Breast epithelium | 006FA |
| Diploid fibroblast | HCS (human corneal stroma), MRC-5 |

[1]The SW1 116, HT-29, SW480, Raji lympboblastoid cells, and the pancreatic lines are obtained from the American Type Culture Collection.

given to the patient post-surgery to treat metastases. In some embodiments, the treatment is done whether or not it is known that the patient has metastases (or where metastases have been detected but the full scope of metastatic disease is not known). In other words, protective therapy of the present invention can be applied to patients after conventional surgery, as well as acute therapy for known metastatic disease.

On the other hand, it is not always possible to remove the primary tumor. It is contemplated in some embodiments where the tumor cells are removed from the patient, that a) standard surgery for the removal of a metastases (or portion thereof) is used. After b) treating the tumor cells ex vivo, using stimulating agents, including thapsigargin and/or thapsigargin-related compounds, so as to create treated tumor cells; c) preparing tumor cell fragments/extracts from said treated tumor cells, and d) introducing said fragments/extracts in vivo into the same patient, it is contemplated that an anti-tumor effect against the primary tumor (as well as residual metastatic disease) is generated. In this manner, embodiments of the present invention can be combined with conventional surgical procedures.

In yet another embodiment, subjects are treated in order to prevent cancer. In a preferred embodiment, subjects at risk for particular cancers (whether because of age, genetic predisposition, exposure to radiation, exposure to smoke, inhalation of particulates, consumption of mutagens, infection of HIV, etc.) are treated. In one embodiment, the present invention contemplates a method comprising: a) providing a patient at risk for developing cancer and a cancer cell line, b) treating cells from said cancer cell line ex vivo with an agent selected from the group consisting of thapsigargin and thapsigargin-related compounds, so as to create treated cancer cells; and c) introducing said cells in vivo into said patient to generate an anticancer preventative effect. Of course, introducing live cancer cells may be unattractive (even though they will die or be destroyed). Therefore, in one embodiment, the present invention contemplates a method comprising: a) providing a patient at risk for developing cancer and a cancer cell line, b) treating cells from said cancer cell line ex vivo with an agent selected from the group consisting of thapsigargin and thapsigargin-related compounds, so as to create treated cancer cells; c) preparing cell fragments/extracts from said treated cancer cells, and d) introducing said fragments/extracts in vivo into said patient to generate an anticancer preventative effect. In this particular embodiment, the cancer cells may be from an established cell line and the fragments/extracts can be viewed as a vaccine. It is not intended that the present invention be limited to a single treatment, i.e. the fragments/extracts (with or without other compounds or components) can be administered at intervals (e.g. once per week, twice per month, once per month, once every six months, once per year, once per five years, once per ten years, etc.) It is not intended that the present invention be limited to the particular type of cancer. A variety of cancer types are contemplated, including but not limited to skin cancer cells, prostate cancer cells, breast cancer cells, cervical cancer cells, uterine cancer cells, pancreatic cancer cells, colon cancer cells, lung cancer cells, bone cancer cells and lymphomas (see Table 1 for a list of illustrative cell lines). In a preferred embodiment, the subjects at risk for cancer are cancer-free at the time of treatment.

The above-described vaccine may be manufactured in volume to treat a population. For example, in one embodiment, disease-free humans over fifty years old (or over fifty-five years old) may be administered the vaccine as a prophylactic, e.g. as a one time vaccine or repeatedly at intervals over time (e.g. every 2-5 years or 5-10 years). Indeed, the population may be treated with a "cocktail" vaccine comprising fragments/extracts of at least two different cancer types (i.e. after treating the cancer cells ex vivo, using stimulating agents, including thapsigargin and/or thapsigargin-related compounds, so as to create treated cancer cells) so as to provide a wider scope of protection against cancer. The different cancer types for the "cocktail" can be selected based on increased incidence in a particular population after a certain age (e.g. increase in colon cancer and prostate cancer after age fifty-five in men; increase in breast cancer and cervical cancer after age fifty-five in women).

In yet another embodiment, stimulating agents, including thapsigargin and/or thapsigargin-related compounds, are administered in vivo. In one embodiment, thapsigargin and/or thapsigargin-related compounds are administered with, in or on a carrier. In a preferred embodiment, thapsigargin is encapsulated in a delivery vehicle. It is not intended that the present invention be limited by the nature of the delivery vehicle. In one embodiment, the delivery vehicle comprises a hydrophobic carrier, e.g. hydrophobic particles, including but not limited to hydrophobic interaction beads (such beads are used as a chromatography reagent) can deliver a powerful inflammatory signal in the presence of thapsigargin and/or thapsigargin-related compounds. In another embodiment, the present invention contemplates liposomes, which are also hydrophobic, as the delivery vehicle.

It is contemplated that the encapsulated thapsigargin (e.g. liposome-encapsulated) can be administered systemically or locally in cancer patients, including but not limited to cancer patients with locally advanced or metastatic cancers. They can be administered intravenously, intrathecally, intraperitoneally, nasally, as well as orally. They may also be introduced by intrapulmonary administration (e.g. via inhalation or an endotracheal tube). They can also be administered through the skin to treat cancer, including skin cancers such as melanoma. They can be administered alone or in combination with other compounds. They can be administered to reduce the metastatic load in the patient prior to surgery; or they can be administered after surgery.

The ex vivo treatment method described above, may have advantages in some cases over direct in vivo administration (e.g. intravenous injection). In the case of ex vivo treatment: 1) thapsigargin contacts the appropriate target cell, namely, cancer cells; 2) exposure in culture allows for the removal of the agents prior to reintroduction of the fragments/extracts in the patient, i.e., the patient is exposed to only very small amounts of thapsigargin in vivo (resulting in minimal toxicity) and 3) lack of systemic exposure to the stimulating antigens reduces the chance of inducing antibodies to thapsigargin.

On the other hand, it is contemplated that there may be instances where direct in vivo administration can be used such that 1) thapsigargin contacts the appropriate target cell, namely, cancer cells; 2) the patient is exposed to only very small amounts of thapsigargin in vivo (resulting in minimal toxicity) and 3) the chance of inducing antibodies to thapsigargin is small. For example, where the tumor(s) is accessible via a procedure selected from the group consisting of endoscopy, bronchoscopy, cystoscopy, colonoscopy, laparoscopy, and catheterization, it may be possible to target cancer cells without exposing the patient to large amount of thapsigargin. Moreover, skin cancers are particularly well-suited to direct in vivo administration of thapsigargin and/or thapsigargin-like compounds (whether in liposome formulations or other hydrophobic formulations). Skin cancers on the surface of the skin can be contacted with thapsigargin in situ. Skin cancers within the skin or just below the skin can be contacted subcutaneously, intradermally, or transdermally. In one embodiment, the present invention contemplates a method comprising a) providing a patient having skin cancer; and b) contacting said skin cancer with thapsigargin. In one embodiment, thapsigargin is applied topically in a cream or ointment. In one embodiment, thapsigargin is applied to the skin via a patch.

With respect to the skin, the present invention contemplates in certain embodiments exposing healthy melanocytes (or dendritic cells) to thapsigargin (e.g. via liposome delivery, a skin patch or the like) so as to trigger a protective anti-cancer immune response. While not limited to a particular mechanism, in such an approach, it is believed that thapsigargin introduced in the vicinity of healthy melanocytes may activate the immune system to inhibit melanoma progression at a distant site (or protect against melanoma formation at a distant site). Regardless of the mechanism, it is experimentally shown (below) that treatment with thapsigargin can be beneficial even when administered at sites distant from the cancer.

The present invention also contemplates other approaches to direct in vivo administration where 1) thapsigargin contacts the appropriate target cell, namely, cancer cells; 2) the patient is exposed to only very small amounts of thapsigargin in vivo (resulting in minimal toxicity) and 3) the chance of inducing antibodies to thapsigargin is small. For example, in one embodiment, the present invention contemplates a targeted approach to direct in vivo administration where 1) thapsigargin is conjugated to a targeting molecule or moiety so that it is brought in contact the appropriate target cell, namely, cancer cells; and thereby 2) the patient is exposed to only very small amounts of thapsigargin in vivo (resulting in minimal toxicity and reducing the chance of inducing antibodies to thapsigargin). It is not intended that the present invention be limited to the targeting molecule or moiety, or the nature of the conjugate. A variety of targeting molecules and moieties are contemplated. In one embodiment, the targeting molecule is an antibody or fragment thereof (Fab, single chain, etc.) and conjugates are made as described by Rodwell et al., U.S. Pat. No. 4,671,958, hereby incorporated by reference and Goers et al., U.S. Pat. No. 4,867,973, hereby incorporated by reference. It is not intended that the present invention be limited by the nature of antibody. Monoclonal antibodies can be used. However, humanized or completely human antibodies are preferred.

It is not intended that the present invention be limited by the nature of the target for the targeting molecule (i.e. nature of the antigen for the antibody). For example, the antibody may target receptors (e.g. estrogen receptors) on human cancer cells or oncogene products on the surface of human cancer cells. On the other hand, the present invention is not limited to antibody targeting. In one embodiment, thapsigargin can be conjugated directly to estrogen and thereby delivered to the estrogen receptors on human cancer cells (without the use of antibodies). Alternatively, thapsigargin can be conjugated to other steroidal androgens (cis-androsterone, estradiol, testosterone, 19-testosterone, and 5-alpha-dihydrotestosterone) or their corresponding peptide analogs. In other embodiments, thapsigargin can be conjugated to growth factors such as epidermal growth factor in a manner similar to that described by Myers et al., U.S. Pat. No. 5,087,616, hereby incorporated by reference.

While not limited to any mechanism, it is believed that exposing cells to thapsigargin and/or thapsigargin-related compounds causes the cancer cells to be immunostimulatory. When administered to subjects having tumors, the extracts preferably induce a tumoricidal reaction resulting in tumor regression. It should be understood that the term, "tumoricidal reaction," as used herein, means that the tumor cells are killed, and is not meant to be limited to any particular method by which tumor cells are killed. For example, it may be that the tumor cells are killed directly (e.g., cell-cell interaction) or indirectly (e.g., release of cytokines like interferon). With respect to cytokines, it is shown herein that the fragments/extracts described above induce cytokine secretion in immune cells.

In one embodiment, the present invention contemplates an in vitro assay for screening compounds for thapsigargin-like immune effects. For example, in one embodiment, the present invention contemplates a method, comprising a) providing cancer cells and a pre-monocytic cell line, said pre-monocytic cell line transfected with a DNA construct encoding a NF-κB promoter driving expression of a marker protein; b) treating said cancer cells in vitro with an agent selected from the group consisting of thapsigargin and thapsigargin-related compounds, so as to create treated cancer cells; c) introducing said treated cancer cells to said pre-monocytic cell line in vitro; and e) measuring the amount of said marker protein. In another embodiment, the present invention contemplates a method, comprising a) providing cancer cells and a premonocytic cell line, said pre-monocytic cell line transfected with a DNA construct encoding a NF-κB promoter driving expression of a marker protein; b) treating said cancer cells in vitro with an agent selected from the group consisting of thapsigargin and thapsigargin-related compounds, so as to create treated cancer cells; c) preparing cell extracts from said treated cancer cells, d) introducing said extracts to said pre-monocytic cell line in vitro; and e) measuring the amount of said marker protein. It is not intended that the screening assay be limited to using only premonocytic cell lines. Monocyte-like cells lines, such as the cell line RAW, may also be used. Moreover, when pre-monocytic cell lines are used, it is not intended that the present invention be limited by the particular cell line; a variety of pre-monocytic cell lines is known including ML1, HL60, and U-937. Preferred pre-monocytic cell lines are the human pre-monocytic cell lines THP-1 and MonoMac-6.

In one embodiment, the ex vivo method is further modified such that the patient is not exposed to said fragments/extracts. Rather, immune cells are exposed to either intact cancer cells or the fragments/extracts ex vivo. For example, patient lymphocytes are removed from the patient and exposed to the treated (i.e. treated with thapsigargin and/or thapsigargin-related compounds) tumor cells or fragment/extracts ex vivo so as to generate stimulated lymphocytes; thereafter, said stimulated lymphocytes are reintroduced to the patient with an anti-cancer therapeutic effect. It is not intended that the invention be limited by the origin or nature of the immune cells. Preferably, they are hematopoietic cells, such as lymphocytes (e.g., tumor infiltrating lymphocytes), macrophages, dendritic cells (and the like) or cells capable of developing into immune cells. While they may be isolated from a variety of sources, such as bone marrow (e.g., from femurs by aspiration), spleen or peripheral blood (e.g., collected with heparin and separated by Ficoll/hypaque gradient), as well as from the tumor (e.g., tumor infiltrating lymphocytes). It is preferred that they are obtained from the lymph nodes. While they may be obtained from normal, disease-free donors, it is also preferred that they be obtained from tumor-bearing hosts.

Definitions

As used herein, a "subject" can be a human or animal. A patient is a human under medical care, whether in the hospital, as an out-patient, in the clinic, or in a doctor's office. A "subject at risk for cancer" and a "patient at risk for cancer" may be at risk for a variety of reasons (whether because of age, genetic predisposition, exposure to radiation, exposure to smoke, inhalation of particulates, consumption of mutagens, infection by HIV, etc.). For example, a person may be at risk because he/she is in a family with a history of cancer. On the other hand, one may be at risk because of the results of a genetic screening assay. With regard to the latter, detection of mutations is an increasingly important area in clinical diagnosis, including but not limited to the diagnosis of cancer and/or individuals disposed to cancer (i.e. at risk). The protein truncation test (PTT) is a technique for the detection of nonsense and frameshift mutations which lead to the generation of truncated protein products. Genes associated with cancer such as human mutL homologue and human nutS homologue (both involved in colon cancer), and BRAC1 (involved in familial breast cancer) can now be screened for mutations in this manner, along with others. Those who are found to have such truncation mutations (as well as other types of mutations) are recognized to be at risk for cancer.

Thapsigargicin and thapsigargin are natural compounds (closely related guaianolides) that can be synthesized or (more commonly) extracted from the roots of *Thapsia garganica* L. Indeed, there are at least 15 closely related guaianolides found in *Thapsia* (see Table 2 below).

TABLE 2

The known range of thapsigargins found in *Thapsia*

| Compound | | $R^1$ | $R^2$ |
|---|---|---|---|
| 1 | Thapsigargin | O-Oct | But |
| 2 | Thapsigargicin | O-Hex | But |
| 3 | Thapsitranstagin | O-iVal | 2-MeBut |
| 4 | Thapsivillosin A | O-Ang | Sen |
| 5 | Thapsivillosin B | O-Anq | 2-MeBut |
| 6 | Thapsivillosin C | O-Oct | 2-MeBut |
| 7 | Thapsivillosin D | O-6-MeOct | Sen |
| 8 | Thapsivillosin E | O-6-MeOct | 2-MeBut |
| 9 | Thapsivillosin G | O-6-MeHep | 2-MeBut |
| 10 | Thapsivillosin H | O-Ang or Sen | Ang or Sen |
| 11 | Thapsivillosin I | O-Ang | But |
| 12 | Thapsivillosin J | O-Ival | But |
| 13 | Thapsivillosin K | O-Sen | 2-MeBut |
| 14 | Trilobolide | H | (S)-2-MeBut |
| 15 | Nortrilobolide | H | But |
| 16 | Thapsivillosin F | H | Sen |

Ang, angeloyl; Sen. senecioyl; iVal, Iso-valeroyl.

These 16 natural compounds fall into two series of molecules differentiated by the presence of an oxygen substituent at the C-2 position. In the trilobolide series of compounds, this substituent is absent. Thapsigargin is commercially available from a number of sources: MP Biomedicals (Irvine Calif.), Sigma, Calbiochem, and Alomone Labs. Thapsigargicin is also commercially available (Calbiochem). Thapsigargin is often referred to as a sesquiterpene

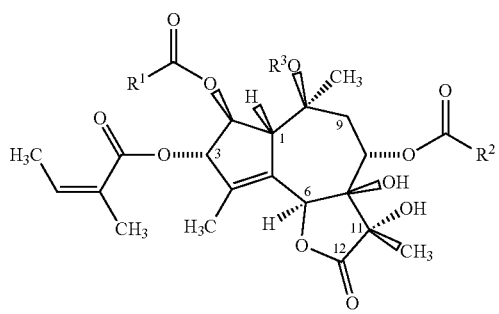

1 $R^1 = (CH_2)_6CH_3$, $R^2 = (CH_2)_2CH_3$, $R^3 = OCCH_3$
2 $R^1 = (CH_2)_6CH_3$, $R^2 = (CH_2)_2CH_3$, $R^3 = H$
3 $R^1 = (CH_2)_4CH_3$, $R^2 = (CH_2)_2CH_3$, $R^3 = OCCH_3$
15 $R^1 = R^2 = (CH_2)_6CH_3$, $R^3 = H$ lactone (see structure 1, below) or sesquiterpene lactone tetraester. Thapsigargin derivatives have been made by a variety of strategies. For example, hydrolysis of the acetyl group at O-10 has been performed to give deacetylthapsigargin (see structure 2, below).

Acetylation of one of the hydroxyl groups and reduction of the lactone carbonyl into a methylene group have also been done. As used herein, "thapsigargin-related compounds" include thapsigargin derivatives, analogues and compounds with similar activity. Thus, natural analogues (see Table 2 above) as well as synthetic analogues (see below) are intended to be within the scope of the present invention. Indeed, sesquiterpenoids generally and guaianolides specifically are intended to be within the scope of the present invention. A number of analogues of thapsigargin have been synthesized by alkylating or acylating O-11 and O-12 in the lactol obtained by reducing thapsigargicin. Introduction of alpha-disposed substituents decreased the Ca(2+)-ATPase inhibitory potency of the analogue, whereas the enzyme was more tolerant toward beta-disposed substituents, indicating that the alpha-face of Scheme

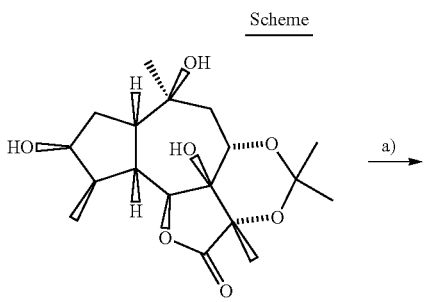

75

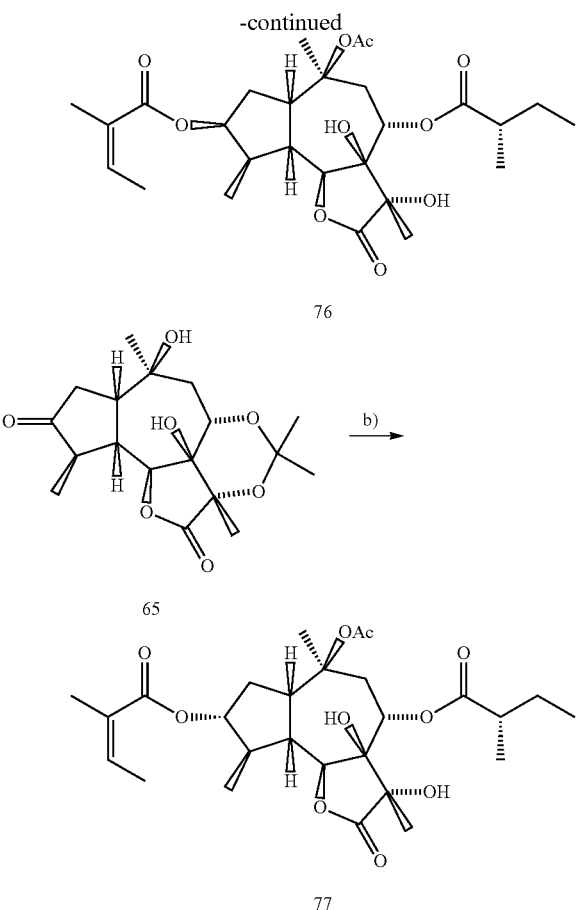

Analog synthesis. a, 1: 2,4,6-trichlorobenzoyl chloride, angelic acid, Et₃N, toluene, 75° C. (85%); 2: isoprenyl acetate, polymer-supported TsOH, 4-Å sieve, DCM, RT (95%); 3: MeOH, 3 M HCl; 4: (S)-2-methyl butyric anhydride, DCM, DMAP, RT (90%, two steps). b, 1: Ac₂O, DMAP, DCM (99%); 2: NaBH₄, MeOH, RT; 3: 2,4,6-trichlorobenzoyl chloride, angelic acid, Et₃N, toluene, 75° C.; 4: MeOH, 3 M HCl, 40° C.; 5: (S)-2-methylbutyric anhydride, DCM, DMAP, RT (60% over four steps).

the lactone ring is in close contact with the binding site when the inhibitor is bound to the enzyme. Some analogues made synthetically have been shown to have potent activity (such as compound 77, below). Other analogues include L12ADT.

With respect to derivatives, the present invention contemplates a variety including but not limited to 8-O-debutanoylthapsigargin, 8-O-(4-aminocinnamoyl)-8-O-debutanoylthapsigargin (termed ACTA). A thapsigargin C8-derivative (ZTG) was synthesized by acylating debutanoyl-thapsigargin with 4-azido[carboxyl-14C]benzoic acid.

With respect to compounds "having similar activity," thapsigargin (TG) is a potent inhibitor of Ca(2+)-ATPase from sarcoplasmic and endoplasmic reticula. Previous enzymatic studies have concluded that Ca(2+)-ATPase is locked in a dead-end complex upon binding TG with an affinity of <1 nM and that this complex closely resembles the E(2) enzymatic state. However, compounds having similar activity need not act through the same mechanism. Drugs that might have similar effects include (but are not limited to): 2, 5-di-(tert-butyl)-1,4-benzohydroquinone, cholecystokinin octapeptide (CCK-8), cyclopiazonic acid, calcium ionophore A23187, 3,3'-Diindolylmethane (DIM), ring-substituted DIMs and 1,1-bis(3'-indolyl)-1-(p-substitutedphenyl) methanes (C-DIMs), N,N-Dimethyl-D-erythro-sphingosine (DMS), Econazole, inositol 1,4,5-trisphosphate, and *Pasteurella multocida* toxin (PMT).

The present invention contemplates, as compositions, cancer cells treated with the above compounds. In a preferred embodiment the present invention contemplates, as compositions, the fragments and/or extracts of these treated cancer cells.

As used herein, an "anticancer therapeutic effect" includes one or more of the following: inhibition of cancer cell growth, increased cancer cell death (a tumoricidal reaction), reduction in tumor invasiveness, reduction in overall tumor burden, reduction in local tumor burden, reduction in size of the primary tumor, prevention of metastases, reduction in the number of metastases, reduction in the size of metastases, and prolonged life. While it is desired that the treatment render the subject free of disease, it is not intended that the present invention be limited to curing cancer. There is therapeutic benefit even if cancer is simply slowed. It is not intended that the present invention be limited to the magnitude of the effect. For example, the reduction in size of the primary tumor (or of a metastases) can be as little as a 10% reduction or as great as a 90% reduction (or more). It is also not intended that the present invention be limited to the duration of the anticancer therapeutic effect. The treatment (using the various embodiments described herein) may result in only temporary inhibition of cancer cell growth, temporary increased cancer cell death, temporary reduction in tumor invasiveness, temporary reduction in overall tumor burden, temporary reduction in local tumor burden, temporary reduction in size of the primary tumor, temporary prevention of metastases, temporary reduction in the number of metastases, or temporary reduction in the size of metastases. The temporary effects may last weeks to months, or months to years. These parameters are relatively easy to measure (e.g a reduction in the size of the primary tumor). With respect to prevention of metastases and prolonging life, these parameters may be measured against patient population data for the particular tumor type, stage, and the like. As used herein, an "anticancer preventative effect" or "protective effect" comprises an effect that reduces the incidence of new cancers. This parameter can be proved in animals and measured in humans on a population basis.

As used herein, "markers" and "labels" are detectable compounds or moieties. They can be enzymes, fluorescent molecules, and the like. Exemplary enzymes include alkaline phosphatase, horseradish peroxidase, beta-galactosidase, glucose oxidase, a bacterial luciferase, an insect luciferase and sea pansy luciferase (*Renilla koellikeri*), all of which can create a detectable signal in the presence of suitable substrates and assay conditions.

The present invention contemplates a variety of types of "liposomes" including but not limited to cationic liposomes. It is not intended that the present invention be limited by the precise composition of such liposomes. In a one embodiment, the liposomes comprise one or more glycolipids. In a preferred embodiment, the liposomes comprise one or more phospholipids.

BRIEF DESCRIPTION OF THE FIGURES

FIG. 3 presents an illustrative list showing the prevalence of cancer cell lines from various tissues known to secrete cytokines following exposure to a thapsigargin related compound.

FIG. 4 presents exemplary data showing that thapsigargin based immunizations reduces tumor growth and improves survival in C57B1/6 mice. Panel A: Tumor growth over time. Short Lines: Saline Controls. Open Circles: Untreated B16 cell extracts. Solid Circles: 2.5 µM B16+TG cell extracts. Panel B: Cell survival over time. Short Lines: Saline Controls. Open Circles: Untreated B16 cell extracts. Solid Circles: 2.5 µM B16+TG cell extracts.

FIG. 5 presents exemplary data showing that thapsigargin based immunizations has no effect on tumor growth in nude mice (Nu/Nu). Panel A (arrows indicate injection site): Mouse 1 and Mouse 2; B16-TG induced inflammation. Mouse 3 and Mouse 4; B16 controls. Panel B: Cell survival over time. Open Circles: Untreated B16 cell extracts. Solid Circles: 2.5 µM B16+TG cell extracts.

FIG. 8 presents exemplary data showing TG-treated HeLa cell extract induction of monocyte differentiation. Panel A: Untreated monocytes having a rounded morphology. Panel B: Treated monocytes having an elongated and flattened morphology (Arrows).

FIG. 10 Panel A presents exemplary data showing the response of 50,000 THP-1 Clone A9 to various TLR ligands as determined by a luciferase reporter system. Y Axis: relative light units (RLU) generated by the chemiluminescent properties of firefly luciferase protein.

FIG. 10 Panel B presents exemplary data showing a thapsigargin (TG) dose response curve using 50,000 THP-1 Clone A9 as determined by a luciferase reporter system. Y Axis: relative light units (RLU) generated by the chemiluminescent properties of firefly luciferase protein. Open Bars: TG alone. Closed Bars: 30,000 TG-treated HeLa cells. Med=Media control.

FIG. 12 (SEQ ID NO:1) shows the nucleotide sequence for CD40L.

FIG. 13 (SEQ ID NOS:2 and 3) shows the CD40L cDNA prepared for ligation into the XbaI restriction site of pVAX1.

EXPERIMENTAL

The following represents certain illustrations and embodiments contemplated by the present invention and are not intended to be limiting.

Example I

Basic Laboratory Procedures

This example provides basic materials and methods that are used in Examples II-VII below. While these particular experiments utilized the specific compounds and techniques, other similar compounds and techniques are also capable of generating similar data.

Cell Lines

The human cervical epithelium cell line HeLa and the mouse B16-F10 melanoma were purchased from American TCC and maintained in Dulbecco's modified eagle's media [D-MEM (Cellgro®, Herndon Va.)] supplemented with 10% fetal bovine serum (Sigma-Aldrich, St. Louis, Mo.). All cell stress/death-related treatments described below were performed using HeLa cells in initial screens. The human promonocytic leukemia THP-1 (ATCC, Manassas Va.) and pro-macrophage MonoMac6 cells were utilized as the reporter antigen presenting cells utilized in this study. Ziegler-Heitbrock et al., "Establishment of a human cell line (Mono Mac 6) with characteristics of mature monocytes" *Int. J. Cancer* 41:456-461 (1988). Both lines were maintained in RPMI-1640 media (Cellgro®) supplemented with 10% fetal bovine serum. Unless otherwise noted, all cells were maintained at 37° C. in a humidified incubator supplemented with 5% $CO_2$.

Compounds

The following list includes the small molecule compounds evaluated in this study: thapsigargin, thapsigargicin (MP Biomedicals, Irvine Calif.), 1,2-bis(o-aminophenoxy)ethane-N,N,N',N'-tetraacetic Acid Tetra(acetoxymethyl) ester [BAPTA-AM, (EMD Biosciences, San Diego, Calif.)], ethyleneglycol-bis(β-aminoethyl)-N,N,N',N'-tetraacetoxymethyl ester [EGTA-AM (EMD Biosciences)], 1,2-bis(2-aminophenoxy)ethane-N,N,N',N'-tetraacetic acid (EGTA), tetrandrine, KCl, Amyloid peptide $A\beta_{1-42}$, 1-Oleoyl-2-acetyl-sn-glycerol (OAG), calcimycin A23187, 2-aminoethyl diphenylborinate (2-APB), histamine, cyclopiazonic acid, 2,5-di-(t-butyl)-1,4-hydroquinone [BHQ (EMD Biosciences)], $GdCl_3$, nicardipine hydrochloride, 1-(o-chloro-α,αdiphenylbenzyl)imidazole (clotrimazole), apamin, charybdotoxin, radicicol, brefeldin A, tunicamycin, tamoxifen, ionomycin, staurosporine, cis-diammineplatinum(II) dichloride (cisplatin), paclitaxel, methotrexate, cycloheximide, and rapamycin. Unless otherwise noted, all compounds were purchased from Sigma-Aldrich. Compounds were dissolved per manufacturer's recommendations prior to addition to HeLa cells in a range of concentrations based on the published literature and incubated between 1 minute to two days. The known mediators of inflammation pam3cys-ser-(lys)4, hydrochloride (Pam3Cys), bacterial flagellin, and lipopolysaccharide were purchased from EMD Biosciences.

DNA Constructs

Figure 13:
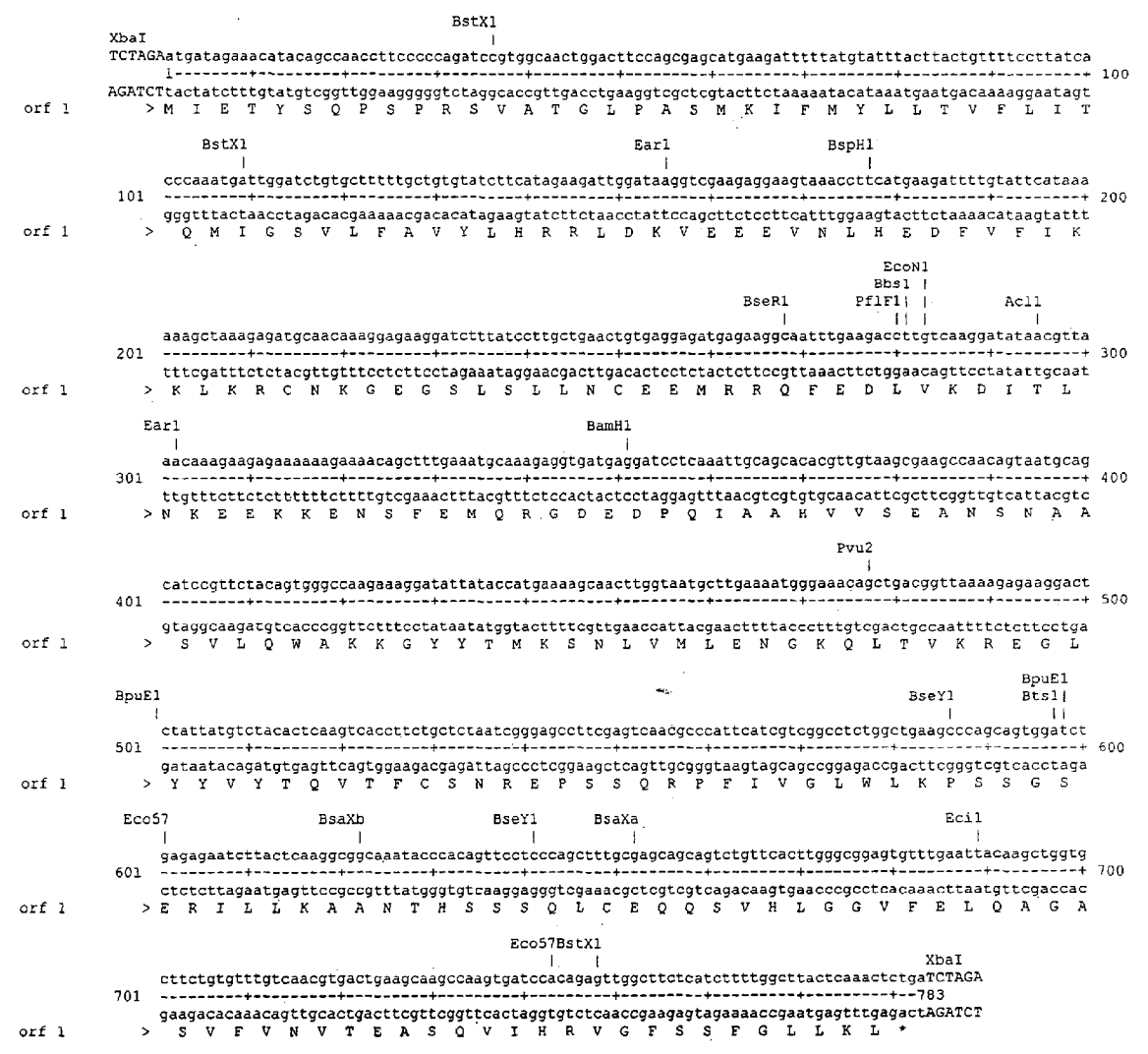
Figure 14:
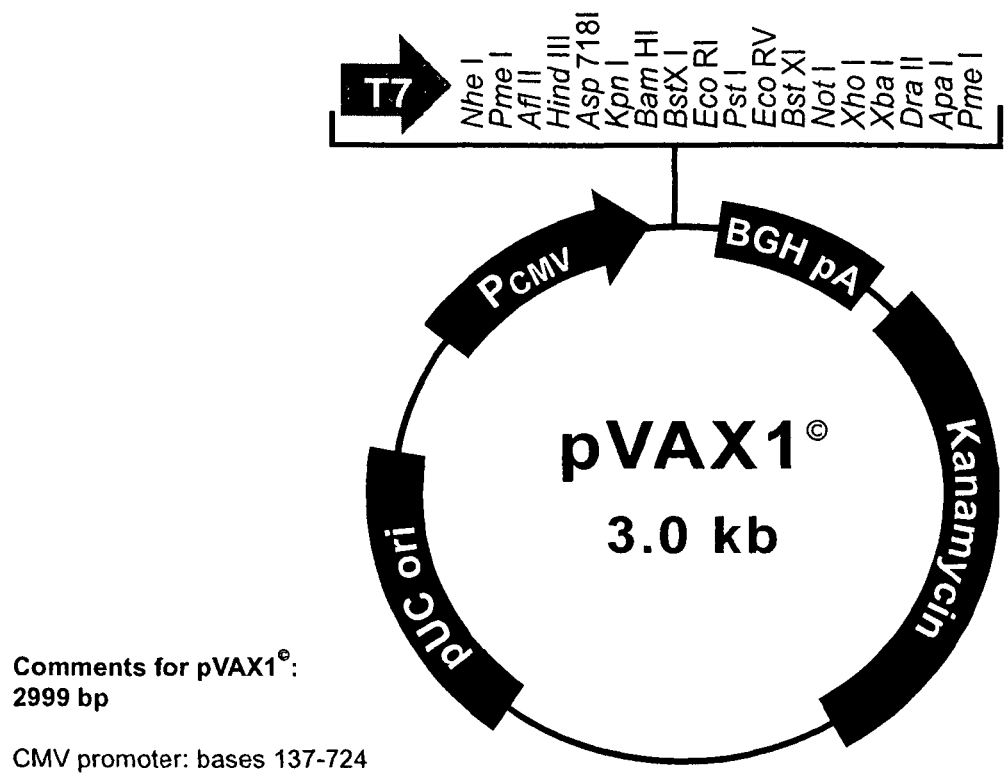
FIG. 14 shows the map for the commercially available pVAX1 expression plasmid.

The cell-death inducing transgenes evaluated include human caspase 8, caspase 9, caspase 3, human insulin growth factor-1 receptor intracellular domain (IGF-1R IC), and neurokinin-1 receptor (NK1R), all cloned into the pcDNA3.1 vector (Invitrogen). The mouse CD40L (or CD 154) expression plasmid was generated by creating the CD40L complimentary DNA using the NCBI published nucleotide sequence of mouse CD40L (FIG. 12) and overlapping oligonucleotides encoding this sequence flanked by Xbal restriction sites (FIG. 13) followed by polymerase chain reaction using Pfu DNA polymerase (Stratagene, San Diego Calif.). The resulting DNA was digested with Xbal (New England Biolabs, Ipswich Mass.) and ligated into a similarly digested pVAX1 expression vector (Invitrogen, Carlsbad Calif.) (FIG. 14). The pVAX-CD40L construct was verified by DNA sequencing.

Transfections

All transfections were performed using HeLa cells and Lipofectamine 2000® transfection reagent (Invitrogen) per manufacturer's suggestions. NK1R-transfected cells were incubated with 1 μM substance P peptide (Sigma-Aldrich) to induce death one day following transfection.

Other Cell Stress/Death Pathways

Serum starvation was performed following incubation of HeLa cells in DMEM without serum for times ranging from 1 to 24 hours. Heat shock was induced by incubating cells at 42-45° C. between 1-6 hours.

Quantification of Pro-Inflammatory Cytokine Release

Following cell stress/death, resulting cells/cell debris were collected, washed 3 times with excess phosphate-buffered saline, rapidly cycled through freeze/thaw (−80° C. to 25° C.) three times, and quantified by UV spectrophotometry (A280). To determine the presence of pro-inflammatory signals within stressed/dead cells, 40 μg of stressed/dead cell were added to 50,000 THP-1 and incubated for 18 hours. Supernatants were assessed for the presence of pro-inflammatory cytokines including tumor necrosis factor-α (TNF-α), interleukin 8 (IL-8), and IL-12 using commercially available ELISA systems.

Generation of Thapsigargin-Dependent Inflammatory Activity

B16-F10 cells were cultured in 150 mm tissue culture plates until ~80% confluent prior to the addition of thapsigargin (2.5 μM). Cells were allowed to incubate for 48 hours prior to collection, three washes in excess phosphate-buffered saline, freeze-thaw cycles, and quantification as described above. Untreated cells were similarly harvested and both extracts were assessed in vitro for inflammatory activity using the THP-1 system described above prior to further use in vivo.

Mouse Immunizations and Tumor Challenge

All of the following mouse studies described were approved by the Buck Institute Institutional Animal Care and Use Committee (IACUC) prior to initiation. 6-8 week old female C57B1/6 and nu/nu mice were purchased from Charles River Laboratories (Wilmington Mass.). Immunizations were performed by injecting 500 μg of B16-F10 extract (with or without thapsigargin treatment) three times at two week intervals by various routes of immunization including subcutaneous, intraperitoneal, and intradermal routes. Live tumor challenge was performed by injecting 100,000 live B16-F10 cells subcutaneously at a contralateral site two weeks following the last booster.

Example II

Identification of a Thapsigargin-Sensitive Endogenous Danger Signal

Figure 1:
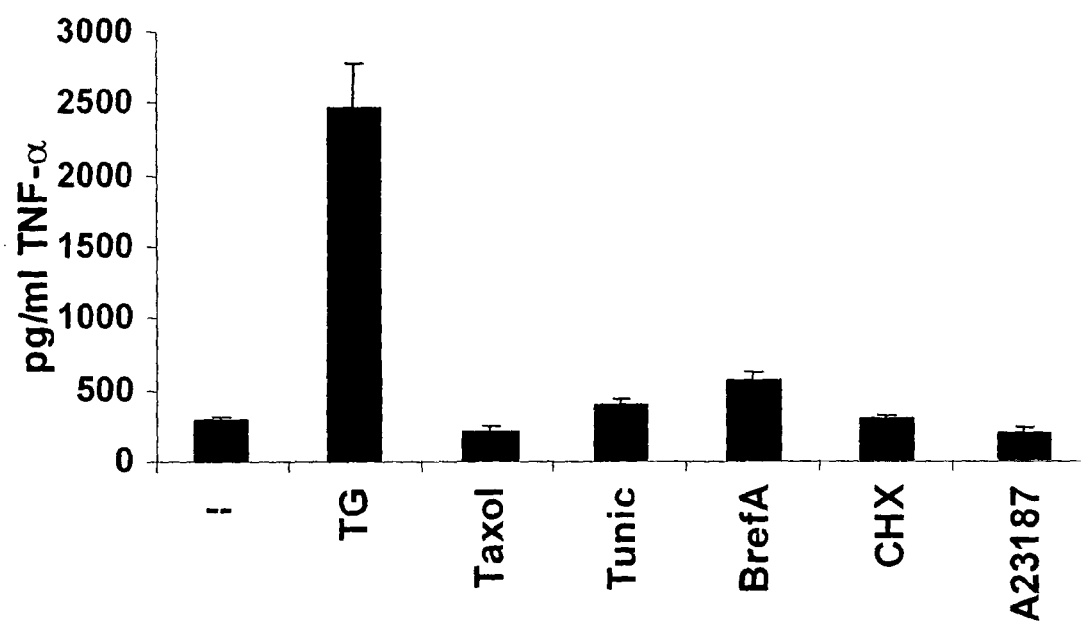
FIG. 1 presents exemplary data showing the effects of various compounds on the proinflammatory activity of cervical cancer HeLa cells. X Axis: control (−); thapsigargin (TG); taxol, tunicamycin (Tunic), brefeldin (BrefA), cycloheximide (CHX), and calcimycin (A23187). Y Axis: TNF-α (pg/ml).

A variety of different potential cell stress and cell death inducing agents were screened. The plant-derived thapsigargin toxin induced TNF-a secretion in a patient-derived cervical cancer cell line (HeLa) and was thus identified for use in the various anti-cancer embodiments described above. In contrast, other potential cellular stressors (i.e., for example, Taxol®, tunicamycin, brefledin A, cycloheximide, and calcimycin) were tested but did not induce immunostimulatory activity. (See FIG. 1).

Thapsigargin was also capable of activating an antigen presenting cell (APC) in a read-out system utilizing a monocytic cell line to secrete large amounts of the inflammatory cytokine tumor necrosis factor-α. (TNF-α). (data not shown).

Example III

Thapsigargin-Induced Secretion of Cytokines

This example illustrates that thapsigargin treatment of cancer cells renders these cells immunostimulatory to antigen presenting cells (monocytes, macrophages, dendritic cells, etc.) which are activated to release cytokines. Although it is not necessary to understand the mechanism of an invention, it is believed that IL-12 plays a role in the development of cell mediated immune responses (the type of immune response that may be necessary for the control of cancer and infection by intracellular pathogens).

Figure 2:
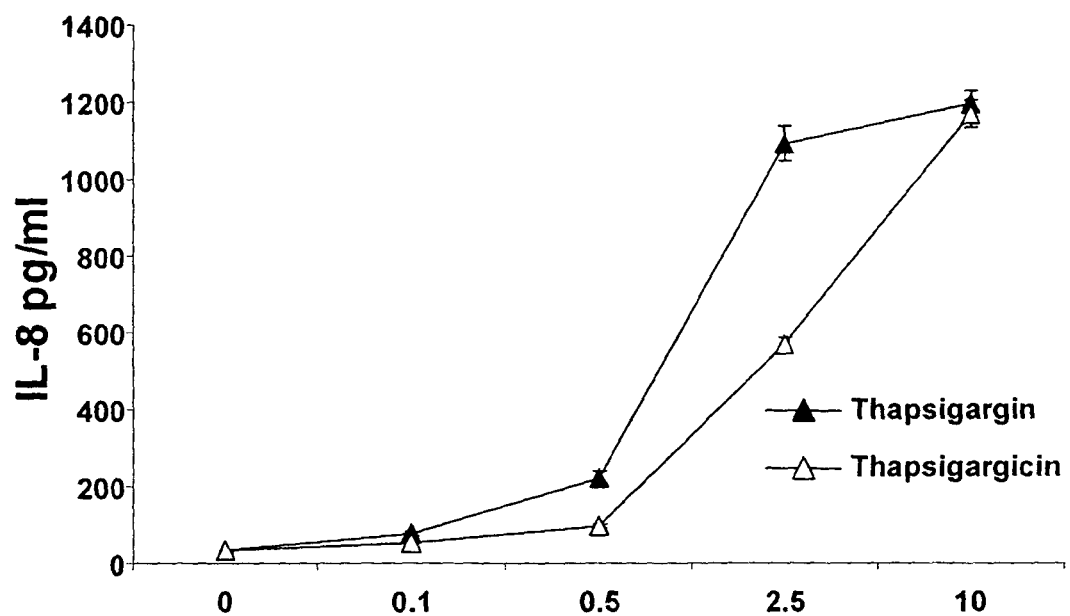
FIG. 2 presents exemplary data showing a comparison of thapsigargin versus thaspigargicin treated HeLa cells in stimulating the release of human IL-8 from the monocyte cell line THP-1. X Axis: thapsigargin or thapsigargicin concentration (µM); Y Axis: Interleukin 8 (IL-8) concentration (pg/ml).

A thapsigargin-related compound thapsigargicin (a less hydrophobic analog of thapsigargin) and thapsigargin activated a dose-dependent secretion of IL-8 from the monocyte cell line THP-1. (See FIG. 2). These data show that thapsigargin-related compounds are capable of activating a potent inflammatory reaction. Thapsigargin treatment also results in secretion of IL-12, IL-8, and TNF-α in a variety of patient-derived cancer lines. (See FIG. 3).

Example IV

In Vivo Immunization with Thapsigargin-Treated B16 Extracts

This example demonstrates that immunization with thapsigargin-treated cells confers protection against cancer progression.

The poorly immunogenic mouse melanoma cell line B16 was treated with thapsigargin in vitro to render it pro-inflammatory (i.e, capable of secreting cytokines in accordance with Example III). Subsequently, mice were immunized with thapsigargin-treated B16 cells (after they were washed, quantified, and lysed by freezing and thawing to create a solution of cell fragments) (B16+TG; 500 µg) and untreated B16 cells (B16) or saline buffer as controls, three times, once every two weeks. Two weeks following the final immunization, mice were implanted with live B16 cancer cells and tumor progression was monitored.

B16+TG induced a transient inflammatory response in C57B1/6 mice at the site of immunization. This response was not seen in the saline solution or B16 groups. The C57B1/6 mice displayed a significantly delayed tumor progression and an improved lifespan after immunization with B16+TG but not after B16 or saline injections. (See FIGS. 4A and 4B, respectively). The data show that the treated animals lived, on average, almost twice as long following tumor grafts.

A similar experiment using nude mice (Nu/Nu) demonstrated that B16+TG (again, after the cells were washed, quantified, and lysed by freezing and thawing to create a solution of cell fragments) was ineffective in improving survival. Thapsigargin-treated cell immunization of nude mice demonstrated a significant in situ inflammation but this was ineffective in controlling tumor progression. (See FIG. 5A and FIG. 5B, respectively). While not necessary to the practice of the present invention, these data are consistent with the hypothesis that nude mice possess a genetic mutation which interferes with normal thymic development, thereby inhibiting the generation of functional T lymphocytes.

Although it is not necessary to understand the mechanism of an invention, it is believed that T lymphocytes, in particular the CD8+ cytotoxic subset, play a role in the destruction of both neoplastic and intracellular pathogen-infected tissues. Taken together, these data indicate that thapsigargin-treated cells activate inflammation which in turn leads to the generation of a protective T cell response in a manner similar to adjuvants.

Example V

Immunoprotective Memory Induced by B16+TG Injections

This example provides one embodiment wherein an immunization with B16+TG (i.e. TG-treated B16 cells that were thereafter washed, quantified, and lysed by freezing and thawing to create a solution of cell fragments) confers long-term protection against injected melanoma.

Figure 6:
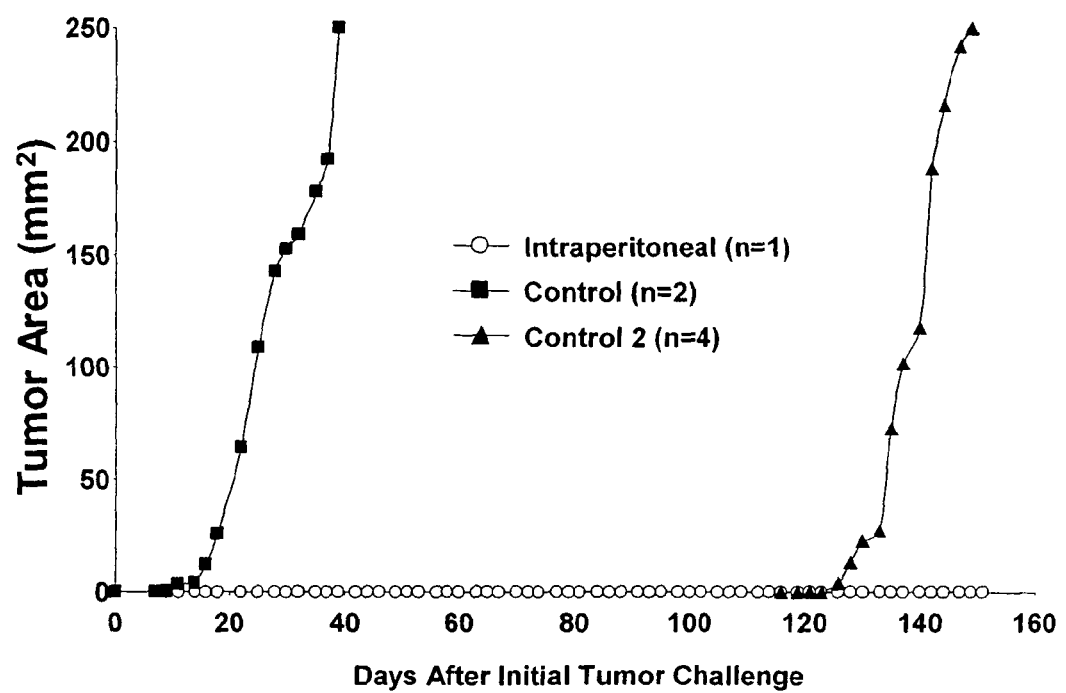
FIG. 6 presents exemplary data showing reduced tumor growth after B16+TG cell extract (500 µg I.P.) immunization of C57B1/6 mice. X Axis: Days After Day 0 B16-F10 melanoma cell injection. Y Axis: Tumor Area (mm$^2$) Open Circles: Two B16+TG cell extract (Day 0 and Day 116) injection and two B16-F10 cell injections (Day 0 and Day 116). Closed Squares: Day 0 untreated control injected with B16-F10 cells. Closed Triangles: Day 116 untreated control injected with B16-F10.

C57B1/6 mice were immunized with B16+TG according to Example VI and subsequently challenged with live B16-F10 melanoma cells. On Day 0 and Day 116 the B16+TG immunized mice did not develop a melanoma tumor. (See FIG. 6). The control mice that had not received the B16+TG extract demonstrated typical tumor progression rates.

Figure 7:
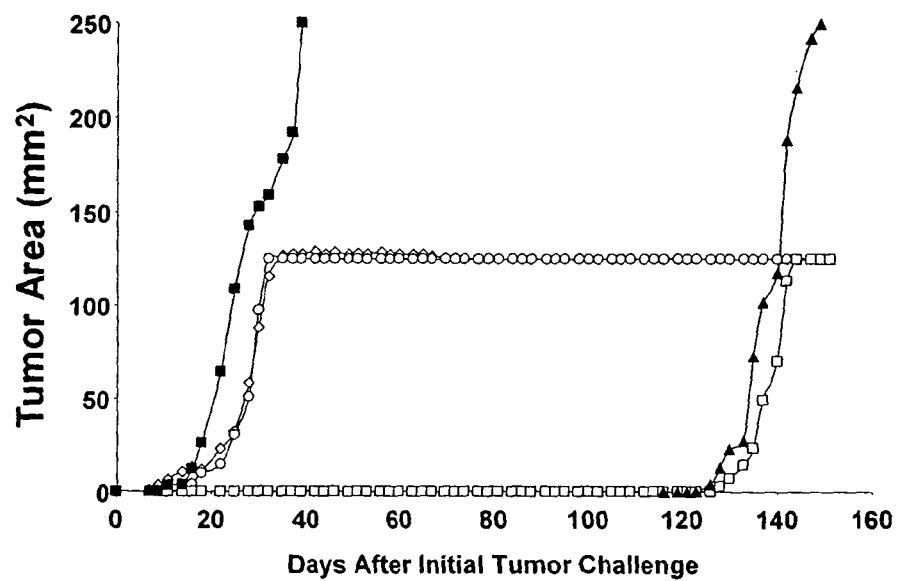
FIG. 7 presents exemplary data showing reduced tumor growth after B16+TG cell extract (500 µg)/CD40L expression plasmid immunization of C57B1/6 mice. X Axis: Days After Day 0 B16-F10 melanoma cell injection. Y Axis: Tumor Area (mm$^2$). Open Circles: Two B16+TG cell extract/CD40L expression plasmid intraperitoneal injections (Day 0 and Day 116) and two B16-F10 melanoma cell injections (Day 0 and Day 116). Open Squares: Two B16+TG cell extract/CD40L expression plasmid intradermal injections (Day 0 and Day 116) and two B16-F10 melanoma cell injections (Day 0 and Day 116). Open Diamonds: Two B16+TG cell extract/CD40L expression plasmid subcutaneous injections (Day 0 and Day 116) and two B16-F10 melanoma cell injections (Day 0 and Day 116). Closed Squares: Day 0 untreated control injected with B16-F10 melanoma cells. Closed Triangles: Day 116 untreated control injected with B16-F10 melanoma cells.

Alternatively, a mouse CD40L expression plasmid was co-immunized with B16+TG extract. When the immunization was performed using intradermal injections complete tumor repression was seen at Day 0. When the immunization was performed using either subcutaneous or intraperitoneal injections a partial tumor repression was seen at Day 0. When the animals given a Day 0 intradermal injection were rechallenged at Day 116, only a partial tumor repression was seen. (See FIG. 7)

These data demonstrate that mice immunized with TG-treated B16 extracts can develop long lasting immunity against B16 melanoma. In this experiment, the extent of this immunity, appears somewhat dependent upon the route of administration. For example, immunizations given intraperitoneally or subcutaneously did not completely suppress tumor growth following B16 melanoma cell injection at either Day 0 or Day 116. (See FIG. 7). However, the conditions have not been optimized.

In conclusion, these data show that B16+TG can protect against a live cancer cell rechallenge over at least a three month period (i.e., 116 days) after the initial immunizations and challenge. These data also suggest that B16+TG extracts may induce the synthesis of pro-inflammatory cytokines such as TNF-a by antigen presenting cells which are likely to activate a transient tumor-specific adaptive immune response by B and/or T cells to delay tumor growth in vivo.

Example VI

Monocyte Differentiation Induced by B16-TG Extracts

This example presents exemplary data as to whether thapsigargin-treated cells are capable of driving the differentiation of monocytes into other subtypes of antigen presenting cells. Previous studies have demonstrated that certain agents act on antigen presenting cells resulting in differentiation into mature dendritic cells. Hertz et al., "Microbial lipopeptides stimulate dendritic cell maturation via Toll-like receptor 2" J. Immunol. 166:2444-2450 (2001). Although it is not necessary to understand the mechanism of an invention, it is believed that dendritic cells are the main cell type responsible for determining whether to activate an adaptive immune response or immune tolerance for any given antigen in the body.

Undifferentiated, rounded, monocytes (See FIG. 8A) were treated with or without thapsigargin-treated HeLa cell extracts for 24 hours. Changes in cellular morphology was then assessed (i.e., for example, induced cellular elongation and/or flattening). The results indicate that thapsigargin-treated cells induce a monocyte cell shape change from primarily rounded to flat and elongated. (See FIG. 8B, indicated by black arrows). This shape change is believed indicative of the maturation process for undifferentiated monocytes which are generally round in morphology into adherent cells with long cellular processes typical of macrophages or immature dendritic cells.

Example VII

Tumor Reduction Induced by a TG Liposomal Formulation

This example presents data showing that thapsigargin-containing liposomes reduce tumor progression in a dose-dependent manner.

Cationic liposomes with a total lipid content of 50 mM containing increasing amounts of thapsigargin (0.0003, 0.003, and 0.03 mol %) were formulated by the lipid film method followed by several cycles of extrusion. Kuntsfeld et al., *Journal of Investigative Dermatology*, 120:476-482 (2003). Liposomes were formulated using various concentrations of thapsigargin, sufficient 1,2-dieoleoyl-sn-glycero-3-phosphocholine (DOPC) to bring the total to 50 mol % and 50 mol % 1,2-dioleoyl-3-trimethylammonium propane (DOTAP) in chloroform. Lipid films were generated following evaporation in a rotary evaporator and re-hydrated in 5% sucrose buffer overnight. Liposomes were extruded using a 200 nM extrusion membrane and stored under argon gas at 4° C. until use. Four groups of two female C57B1/6 mice were simultaneously grafted with 1×10$_5$ live B16-F10 melanoma cells subcutaneously on the left flank on day 0. Mice receiving liposome-encapsulated thapsigargin were injected intradermally with 50 µl of each thapsigargin-containing liposome formulation following tumor implantation on days 7, 8, 9, 14, 15, 16, 21, 22, and 23 at distal sites ranging from the base of the tail to the right flank and tumor progression monitored.

Figure 9:
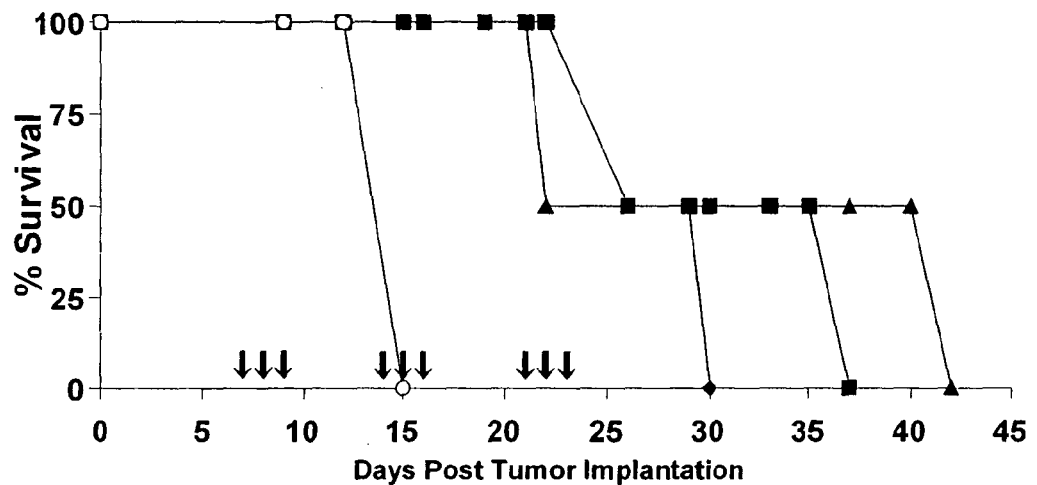
FIG. 9 presents exemplary data showing a dose-dependent improvement of C57B1/6 mice survival following liposomal formulations of TG administered on Days 7, 8, 9, 14, 15, 16, 21, 22, and 23 (arrows). Open Circles: Untreated Control after B16-F10 cell Day 0 injection (S.C.). Closed Diamond: 0.003 mole % TG (I.D.) after B16-F10 cell Day 0 injection (S.C.). Closed Square: 0.003 mole % TG (I.D.) after B16-F10 cell Day 0 injection (S.C.). Closed Triangle: 0.03 mole % TG (I.D.) after B16-F10 cell Day 0 injection (S.C.).

Four groups of two female C57B1/6 mice were then simultaneously grafted with 1×10$^5$ live B16-F10 melanoma cells subcutaneously on the left flank on day 0. Mice receiving liposome-encapsulated thapsigargin were injected intradermally with 50 µl of each thapsigargin-containing liposome formulation on days 7, 8, 9, 14, 15, 16, 21, 22, and 23 at distal sites ranging from the base of the tail to the right flank and tumor progression monitored. The data indicate that liposome-encapsulated thapsigargin is capable of decreasing tumor progression in a dose-dependent manner. (See FIG. 9).

Example VIII

Toxin-Induced NF-κB Promoter Systems

This example presents one embodiment of a toxin-sensitive high-throughput reporter (i.e. marker or label) system.

A stably transfected DNA construct encoding a NF-κB promoter driving firefly luciferase expression was integrated into: i) human pre-monocytic cell line THP-1; and ii) human premonocytic cell line MonoMac-6. Briefly, DNA encoding a concatemerized NF-κB response element upstream of the firefly luciferase gene [Ting et al., "RIP mediates tumor necrosis factor receptor 1 activation of NF-kappaB but not Fas/APO-1-initiated apoptosis" EMBO J. November 15; 15(22):6189-96(1996)] was subcloned into the pEAK8 vector backbone (Edge Biosystems, Gaithersburg Md.) by standard molecular biology techniques. Electroporations were performed using 10 µg of DNA and 700,000 THP-1 or MonoMac6 cells using a Biorad Gene Pulser II electroporator (Biorad, Hercules Calif.), 0.4 cm electrocuvettes, and 200 V, 950 µF. Following electroporation, cells were allowed to recover for two days prior to selection with 300 ng/ml puromycin aminonucleoside (Sigma-Aldrich) for the generation of stably transfected clones. Luciferase expression was quantified using a Top Count NXT luminometer (Perkin Elmer, Wellesley Mass.). Briefly, 50,000 reporter cells were incubated with indicated concentrations of the mediators of inflammation listed for 18 hours in 96-well white plates prior to harvest and analysis.

THP-1 Clone A9

The THP-1-derived clone A9 recognition of the TLR ligands Pam-3-Cys (signaling through TLR2) and bacterial flagellin (signaling through TLR5), but not bacterial lipopolysaccharide (signaling through TLR4) was determined by monitoring NF-κB activity in 96-well white plate automated assays during TG incubation. (See FIG. 10A).

Varying concentrations of thapsigargin were also used in the presence or absence of pre-plated HeLa cells. These results demonstrated that Clone A9 recognized thapsigargin-treated HeLa cells at synergistically greater levels than either untreated HeLa cells or thapsigargin alone. (See FIG. 10B).

Together, these data support the use of Clone A9 in the identification of novel compounds and/or factors which modulate inflammation through TLR2.

MonoMac-6 Clone C5

Figure 11:
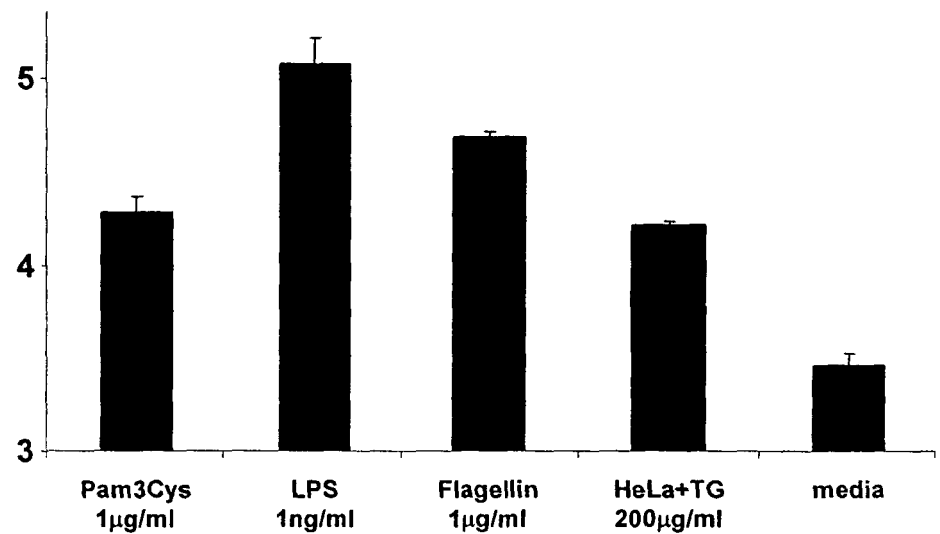
FIG. 11 presents exemplary data showing the response of MonoMac-6 Clone 5 to various TLR ligands as determined by a luciferase reporter system. Y Axis: relative light units (RLU) generated by the chemiluminescent properties of firefly luciferase protein. TG (2.5 µM). Media=Control.

A second stable NF-κB reporter construct transfectant was created using MonoMac-6 cells. In contrast to Clone A9, MonoMac-6 derived clone C5 demonstrated improved recognition of bacterial lipopolysaccharide. Clone C5 also recognized Pam3Cys, flagellin, and thapsigargin-treated HeLa cells. (See FIG. 11).

We claim:

1. A method of quantifying immunostimulation of cancer cells, comprising:

providing cancer cells and pre-monocytic cells, wherein the pre-monocytic cells are cells transfected with a DNA construct comprising a gene encoding a marker protein and an NF-κB promoter that drives expression of the marker protein;

treating the cancer cells in vitro with an immunostimulant so as to create treated cancer cells;

preparing cell fragments or an extract from said treated cancer cells, and contacting the pre-monocytic cells with the fragments or the extract in vitro; and measuring an amount of the marker protein formed in the expressed pre-monocytic cells.

2. The method of claim 1 wherein the immunostimulant is an inhibitor of a Ca(2+)-ATPase from sarcoplasmic and endoplasmic reticula.

3. The method of claim 1 wherein the immunostimulant is selected from the group consisting of thapsigargin, thapsigargicin, thapsitranstagin, a thapsivillosin, trilobolide, and nortrilobolide.

4. The method of claim 1 wherein the immunostimulant is encapsulated in a delivery vehicle.

5. The method of claim 1 wherein the step of preparing cell fragments is performed using at least one of freeze/thawing the cells, exposing the cells to a lysis agent, exposing the cells to a detergent, exposing the cells to an enzyme, and sonicating the cells.

6. The method of claim 1 wherein the cancer cells are skin cancer cells, prostate cancer cells, breast cancer cells, cervical cancer cells, uterine cancer cells, pancreatic cancer cells, colon cancer cells, lung cancer cells, bone cancer cells, or lymphoma cells.

7. The method of claim 1 wherein the cancer cells are surgically removed from a patient.

8. The method of claim 1 wherein the cancer cells are from an established cell line.

9. The method of claim 1 wherein the marker protein comprises firefly luciferase.

10. The method of claim 1 wherein the pre-monocytic cell is selected from the group consisting of ML1, HL60, and U-937.

11. The method of claim 1 wherein the pre-monocytic cell is selected from human pre-monocytic cell line THP-1 and human pre-monocytic cell line MonoMac-6.

12. The method of claim 1 wherein the pre-monocytic cell is replaced by a monocyte-like cell.

13. The method of claim 1, wherein the immunostimulant is encapsulated in a delivery vehicle, and wherein the pre-monocytic cell is selected from human pre-monocytic cell line THP-1, and human pre-monocytic cell line MonoMac-6.

* * * * *